(12) United States Patent
Scherer et al.

(10) Patent No.: US 12,154,250 B2
(45) Date of Patent: Nov. 26, 2024

(54) METHOD FOR PROVIDING AN IMAGE REPRESENTATION BY MEANS OF A SURGICAL MICROSCOPE, AND SURGICAL MICROSCOPE

(71) Applicant: Carl Zeiss Meditec AG, Jena (DE)

(72) Inventors: Dominik Scherer, Aalen (DE); Senay Karaali, Ulm (DE); Selamawit Getachew Kelemu, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 429 days.

(21) Appl. No.: 17/709,388

(22) Filed: Mar. 30, 2022

(65) Prior Publication Data

US 2022/0318969 A1 Oct. 6, 2022

(30) Foreign Application Priority Data

Mar. 30, 2021 (DE) ...................... 10 2021 203 187.0

(51) Int. Cl.
*G06T 5/00* (2024.01)
*A61B 90/00* (2016.01)
(Continued)

(52) U.S. Cl.
CPC .............. *G06T 5/20* (2013.01); *A61B 90/20* (2016.02); *A61B 90/361* (2016.02); *G02B 21/0012* (2013.01); *G02B 21/367* (2013.01); *G06T 5/50* (2013.01); *G06T 2207/10024* (2013.01); *G06T 2207/10064* (2013.01); *G06T 2207/20024* (2013.01); *G06T 2207/20221* (2013.01)

(58) Field of Classification Search
None
See application file for complete search history.

(56) References Cited

U.S. PATENT DOCUMENTS 10,849,712 B2 12/2020 Sugie et al.
2009/0236541 A1* 9/2009 Lomnes ............... A61B 1/0646
250/362
(Continued)

FOREIGN PATENT DOCUMENTS

| CN | 112037216 A | 12/2020 |
| DE | 112016004455 T5 | 8/2018 |
| EP | 3616596 A2 | 3/2020 |

OTHER PUBLICATIONS

Office Action issued in German Patent Application No. DE 10 2021 203 187.0, dated Oct. 4, 2021 (from which this application claims priority) and English language translation thereof.

*Primary Examiner* — Dung D Tran
(74) *Attorney, Agent, or Firm* — Ewers IP Law PLLC; Falk Ewers (57) ABSTRACT

A method for providing an image representation with a surgical microscope, includes capturing a color image representation of a capture region with a camera, capturing a fluorescence image representation of the capture region with a fluorescence camera, generating a detailed image from the captured color image representation with a spatial filter and an edge stop function, mixing the captured color image representation, the captured fluorescence image representation and the generated detailed image to form a mixed image representation, and providing an image signal which encodes the mixed image representation. Further, the disclosure relates to a surgical microscope.

12 Claims, 4 Drawing Sheets

(51) Int. Cl.
  *A61B 90/20* (2016.01)
  *G02B 21/00* (2006.01)
  *G02B 21/36* (2006.01)
  *G06T 5/20* (2006.01)
  *G06T 5/50* (2006.01)

(56) References Cited

U.S. PATENT DOCUMENTS

| | | |
|---|---|---|
| 2016/0007856 A1 | 1/2016 | Ishihara |
| 2016/0324420 A1* | 11/2016 | Zhu .......................... A61B 6/00 |
| 2017/0014022 A1 | 1/2017 | Tamura et al. |
| 2018/0364470 A1 | 12/2018 | Jauger et al. |
| 2019/0274518 A1* | 9/2019 | Themelis ................. A61B 8/12 |
| 2021/0294084 A1* | 9/2021 | Yamaguchi ...... A61B 1/000095 |
| 2022/0151474 A1* | 5/2022 | Sato ....................... A61B 1/046 |

* cited by examiner

METHOD FOR PROVIDING AN IMAGE REPRESENTATION BY MEANS OF A SURGICAL MICROSCOPE, AND SURGICAL MICROSCOPE

CROSS REFERENCE TO RELATED APPLICATIONS

This application claims priority to German patent application DE 10 2021 203 187.0, filed Mar. 30, 2021, the entire content of which is incorporated herein by reference.

TECHNICAL FIELD

The disclosure relates to a method for providing an image representation with a surgical microscope and to a surgical microscope.

BACKGROUND

Distinguishing tumor tissue from non-tumor tissue is one of the main problems when performing surgery on tumors, in particular in the region of the brain. In addition to the information from captured color image representations (white light image representations), surgical microscopes can also capture fluorescence image representations in this respect, wherein fluorescing contrast agents in the tissue are excited by specific excitation during the capture so that the tumor tissue is rendered visible, and marked, in the captured fluorescence image representation. In the process, a captured white light image representation and a captured fluorescence image representation can be overlaid or mixed. However, disadvantageously, detailed information items (e.g., relating to brain vessels or sulci structures in the brain) may be lost.

US 2018/0364470 A1 describes a microscopy system and a microscopy method for recording a fluorescence image and a white light image. Such a microscopy system includes an illumination apparatus for illuminating an object region and for exciting at least one fluorescent dye, an optical unit for imaging the object region on at least one fluorescence image detector and at least one white light image detector. A beam splitter and a filter are arranged in the beam path provided by the optical unit and are configured such that substantially only the fluorescence emitted by the fluorescence dyes is incident on the fluorescence image detector and an image that is as color neutral as possible is recorded by the white light image detector.

US 2016/0007856 A1 describes a fluorescence observation apparatus, including a light source configured to irradiate an object with white light and excitation light; and a processor including hardware, the processor being configured to implement the following: a fluorescence image production unit and a white light image production unit which are configured to produce a fluorescence image and a color white light image, respectively; a state adjustment unit which is configured to adjust weights on an individual basis for a plurality of color component images that form the white light image; and a combination unit which is configured to combine at least one color component image to which the fluorescence image has been added, and the other color component images while the weights are applied, and the condition adjustment unit which is configured to adjust the weights on the basis of the color component images so that the weight for the color component image to which the fluorescence image is added is larger than the weight for the other color component images.

SUMMARY

It is an object of the disclosure to provide a method for providing an image representation with a surgical microscope, and a surgical microscope, in the case of which the mixing of a color image representation and a fluorescence image representation is improved, and in the case of which details in particular are maintained in the mixed image representation.

The object is achieved by a method for providing an image representation with a surgical microscope and a surgical microscope as described herein.

It is a general concept of the disclosure to generate a detailed image from a captured color image representation, which may also be referred to as white light image representation or RGB image representation in particular, said detailed image being additionally mixed into the mixed image representation. In this context, the detailed image is generated from the captured color image representation with a spatial filter, in particular a two-dimensional spatial filter, and an edge stop function. This renders it possible to extract relevant details from the color image representation and additionally consider these when mixing the captured color image representation and the captured fluorescence image representation. Then, the extracted details are still easy to identify in the mixed image representation.

In particular, a method for providing an image representation with a surgical microscope is provided, the method including: capturing a color image representation of a capture region with a camera, capturing a fluorescence image representation of the capture region with a fluorescence camera, generating a detailed image from the captured color image representation with a spatial filter and an edge stop function, mixing the captured color image representation, the captured fluorescence image representation and the generated detailed image to form a mixed image representation, and providing an image signal which encodes the mixed image representation.

Further, a surgical microscope in particular is provided, including a camera which is configured to capture a color image representation of a capture region, a fluorescence camera which is configured to capture a fluorescence image representation of the capture region, and an evaluation device, the evaluation device being configured to extract a detailed image from the captured color image representation with a spatial filter and an edge stop function, to mix the captured color image representation, the captured fluorescence image representation and the extracted detailed image to form a mixed image representation, and to provide an image signal which encodes the mixed image representation.

The method and the surgical microscope are advantageous in that details of the captured color image representation still are contained even in the case of an image representation that has been mixed from the captured color image representation and the captured fluorescence image representation. In particular, the method and the surgical microscope allow the details to be highlighted in the mixed image representation. In particular, vessels and sulci structures in the brain can thus still be rendered clearly and easily visible in the mixed image representation even after mixing. A surgeon and/or assistants can register these details better as a result and information present in the captured color image representation and in the captured fluorescence image representation can be optimally represented. An operational sequence and a workflow during surgery can be improved as a result.

The surgical microscope in particular includes a light source for illuminating the capture region, in which an object to be captured, in particular a body part of a patient, is arranged, with light, in particular white or broadband light. Further, the surgical microscope may also include an (additional) excitation light source for exciting a fluorescence dye. The surgical microscope may further include optical elements, in particular for focusing and/or magnification purposes. The optical elements may also be part of the camera(s). Further, a beam splitter may be arranged in a beam path of the surgical microscope in order, for example, to guide light from the capture region to both the camera and the fluorescence camera. Further, optical filters may also be used when capturing fluorescence image representations.

In particular, provision is made for the spatial filter to be configured as a smoothing filter without creating additional artifacts in the process. In this case, the edge stop function is used in particular to prevent or reduce excessive smoothing effects at edges. In particular, the detailed image is produced by virtue of the captured color image being filtered with the spatial filter, in particular the smoothing filter, while taking account of the edge stop function. The detailed image arises in particular from a difference between the captured color image representation and the color image representation filtered in this way.

In particular, the camera is in the form of a color image detector or white light image detector, that is to say that the camera is configured in particular to capture light in the wavelength range of white light, for example in the wavelength range of visible light. The camera produces and in particular provides a signal which represents an intensity distribution of the light incident on the camera from the capture region, that is to say a color image representation (or white light image representation or RGB image representation). In particular, the color image representation is polychromatic. The camera may include optical elements (lenses, mirrors, beam splitters, optical filters, etc.) for focusing and/or magnification purposes and/or for beam guidance.

In particular, the fluorescence camera is in the form of the fluorescence image detector, that is to say that the fluorescence camera is configured to capture light in the emission wavelength range of at least one fluorescence dye in the capture region with spatial resolution. The fluorescence camera produces and in particular provides a signal which represents an intensity distribution of the light incident on the fluorescence camera, that is to say a fluorescence image representation. In particular, the fluorescence image representation is monochromatic. The fluorescence camera may include optical elements (lenses, mirrors, beam splitters, optical filters, etc.) for focusing and/or magnification purposes and/or for beam guidance and/or filtering.

During mixing, provision can be made for monochromatic image information to be converted into a polychromatic color space or a polychromatic color model, for example if a monochromatic image information item should be mixed to a polychromatic image information item.

The image signal may have both an analog form and a digital form. In particular, the image signal may also be provided in the form of a digital data packet which is saved in a volatile or nonvolatile memory or storage medium and/or which is output via an interface configured to this end.

The mixed image representation or the image signal can be displayed on a display device.

Parts of the surgical microscope, in particular the evaluation device, can be designed, either individually or together, as a combination of hardware and software, for example as program code that is executed on a microcontroller or microprocessor. However, provision can also be made for parts to be designed as application-specific integrated circuits (ASICs) and/or field-programmable gate arrays (FPGAs), either individually or together. In particular, the evaluation device may include at least one computing device and at least one memory.

In an exemplary embodiment, provision is made for an intensity image to be produced from the captured color image representation, the detailed image being produced from the produced intensity image. As a result, a computing power required for the production of the detailed image can be reduced, and so producing the detailed image can be carried out particularly efficiently. By way of example, provision can be made for the captured color image representation (RGB image representation) to be converted into the YCbCr color space and for subsequently only the luminance channel Y, which corresponds to the intensity in particular, to be considered. This can be done with the following MATLAB code, for example:

```
img_ycbcr=rgb2ycbcr(img_rgb); % Convert RGB
    image representation to YCbCr img_Y=img_ycbcr(:,:,1);% Extract intensity informa-
    tion
```

However, other intensity representations may also be used as a matter of principle. By way of example, provision can alternatively also be made of processing at least one color channel of the color image representation (RGB image representation) on an individual basis and of using this as intensity information. If a plurality of color channels are processed on an individual basis, a detailed image can be produced for each of the color channels. The produced detailed images can subsequently be merged, for example mixed, and can continue to be used in mixed fashion in the method.

In an exemplary embodiment, provision is made for the intensity image to be produced and/or processed on a logarithmic scale. As a result, the spatial filter in particular can be implemented particularly efficiently in relation to a required computing power. Building on the MATLAB code specified above, the conversion into the logarithmic representation can be implemented with the following MATLAB code, for example:

```
img_Y_log=log 10(double(img_Y)/255); % Convert
    into log representation
```

In an exemplary embodiment, provision is made for the spatial filter to be a two-dimensional Gaussian spatial filter. The two-dimensional Gaussian spatial filter produces a smoothing effect without producing additional artifacts in the process.

In an exemplary embodiment, provision is made for a position-related value of a gradient of an intensity in the produced intensity image to be used in each case as input parameter of the edge stop function. In particular, such a gradient of the intensity is determined for each position of the intensity image, that is to say for each pixel or pixel-by-pixel. To this end, the following measure for example can be used, where x and y each denote coordinates of the considered pixel:

$$\|\nabla I(x,y)\| = \sqrt{\nabla_x^2(x,y) + \nabla_y^2(x,y)}$$

In an exemplary embodiment, provision is made for the detailed image to be produced by weighted summation of the captured color image representation filtered with the spatial filter and the captured color image representation, followed by a subtraction of the summation image representation from the captured color image representation, with an output value of the edge stop function being used as weighting parameter. In this way, the details are extracted from the color image and provided as detailed image. By way of example, it is possible to define the following edge stop function:

$$w_r = \begin{cases} \left(1 - \left(\frac{x}{\lambda}\right)^2\right)^2, & (x \leq \lambda) \\ 0, & (x > \lambda) \end{cases}$$

Here, x is the value of the gradient that was determined with the aforementioned measure, in particular at the respective pixel. In this case, the parameter $\lambda$ allows the sensitivity of the edge stop function to be adjusted, by way of example $\lambda=0.6$.

The summation is subsequently carried out:

$$(1-w_r) \cdot l_f + w_r \cdot l_{n|}$$

Here, $l_f$ is the intensity value from the captured color image representation and $l_{n|}$ is the intensity value from the captured color image representation filtered with the spatial filter, in particular the two-dimensional spatial filter, more particularly the two-dimensional Gaussian spatial filter. The summation is implemented pixel-by-pixel in particular, where the weighting parameter $w_r$ is chosen or calculated for the respectively considered pixel (in particular with the coordinates x, y; see above).

The summation image representation obtained hereby is subtracted from the captured color image representation, in particular pixel-by-pixel. If the intensity is used, this is carried out in particular using the intensity image and the intensity image filtered with the spatial filter.

In an exemplary embodiment, provision is made for the production of the detailed image to be repeated iteratively with altered parameters. In particular, this allows the iterative use of different parameters, for example in order to obtain certain target criteria. In particular, the individual iteration steps are independent of one another in this case. However, at least one termination condition is monitored during the iteration. By way of example, the iteration is terminated if the following termination condition for the gradient of the intensity of the captured color image representation is satisfied:

$$\|\nabla l_f\| < k | l_n - l |$$

because otherwise a smoothing effect of the spatial filter may become too strong. Independent of this termination condition, provision can be made for the iteration to be terminated if a certain number of iterations have been run through without the termination condition being satisfied (e.g., after 12 iterations, etc.).

In principle, there are three options for the possible implementation of the mixing of the captured color image representation, the captured fluorescence image representation and the produced detailed image to form a mixed image representation.

In the first option, the captured color image representation and the captured fluorescence image representation are typically mixed first and the produced detailed image is subsequently added. In particular, the monochromatic fluorescence image representation can be converted into a polychromatic color space or a polychromatic color model before mixing. Alternatively, it is also possible to assign fixed colors or polychromatic colors (on the basis of an intensity distribution).

In the second option, the produced detailed image is typically added to the captured color image first and the color image representation enriched in this way is subsequently mixed with the fluorescence image representation. Especially when using an intensity image for producing the detailed image, it is advantageous to convert the produced (monochromatic) detailed image into a polychromatic color space or a polychromatic color model prior to mixing with the captured color image.

In an exemplary embodiment, which represents the third option, provision is made, during mixing, for the produced detailed image to be mixed with the fluorescence image representation and for the resultant enriched fluorescence image representation to be mixed with the captured color image representation. If the detailed image was produced from an intensity image, the information in the produced detailed image is located within a monochromatic color space (intensity image). This means that the produced detailed image is compatible with the fluorescence image representation which is also monochromatic. If the produced detailed image is (initially) mixed with the fluorescence image representation, it is possible as a result to avoid errors and artifacts, in particular at edges, which would be visible in the non-monochromatic color space. This can improve quality of the mixed image representation.

In an exemplary embodiment, provision is made for a geometric distortion correction and/or a shading correction to be carried out for the camera and the fluorescence camera. As a result, the captured color image representation and the captured fluorescence image representation can be aligned and/or scaled with respect to one another such that a respectively contained image content is overlaid in the mixed image representation. In particular, defects possibly present in a beam path and in an imaging optical unit of the camera and of the fluorescence camera can be compensated (electronically) hereby if this cannot be implemented, or is not implemented, by optical methods or optical elements.

In a further exemplary embodiment, provision is made for an image improvement and/or an image enrichment to be carried out. By way of example, a measure for improving the contrast may be implemented. Likewise, the fluorescence image representation may be color coded, as a result of which the information from the fluorescence image representation is better identifiable in a mixed image representation. To this end, there may also be color coding on the basis of the intensity values ("pseudo-coloring"). An image enrichment may further include the identification and marking of a boundary of a tumor in the captured fluorescence image representation.

In an exemplary embodiment, provision is made for the method to be carried out on a stereoscopic camera and/or stereoscopic fluorescence camera. As a result, it is possible to produce and provide a stereoscopic mixed image representation, which allows a surgeon and/or an assistant to stereoscopically register the capture region. The method may be carried out accordingly for each of the channels (left and right).

Further features relating to the configuration of the surgical microscope arise from the description of configurations of the method. Here, the advantages of the surgical microscope are respectively the same as in the configurations of the method. In particular, the evaluation device of the surgical microscope is configured to carry out the additional features of the exemplary embodiments of the method.

Further, a method for providing an image representation for a surgical microscope is also provided, the method including: receiving a color image representation of a capture region captured with a camera, receiving a fluorescence image representation of the capture region captured with a fluorescence camera, producing a detailed image from the received color image representation with a spatial filter and an edge stop function, mixing the received color image representation, the received fluorescence image representation and the produced detailed image to form a mixed image representation, and providing an image signal which encodes the mixed image representation. The method can be carried out with a data processing device, including in particular at least one computing device and at least one memory.

Further features for configuring the method for providing an image representation for a surgical microscope emerge from the description of configurations of the method for providing an image representation with a surgical microscope. The advantages of the method are the same in each case.

BRIEF DESCRIPTION OF THE DRAWINGS

The disclosure will now be described with reference to the drawings wherein.

DESCRIPTION OF EXEMPLARY EMBODIMENTS

Figure 1:
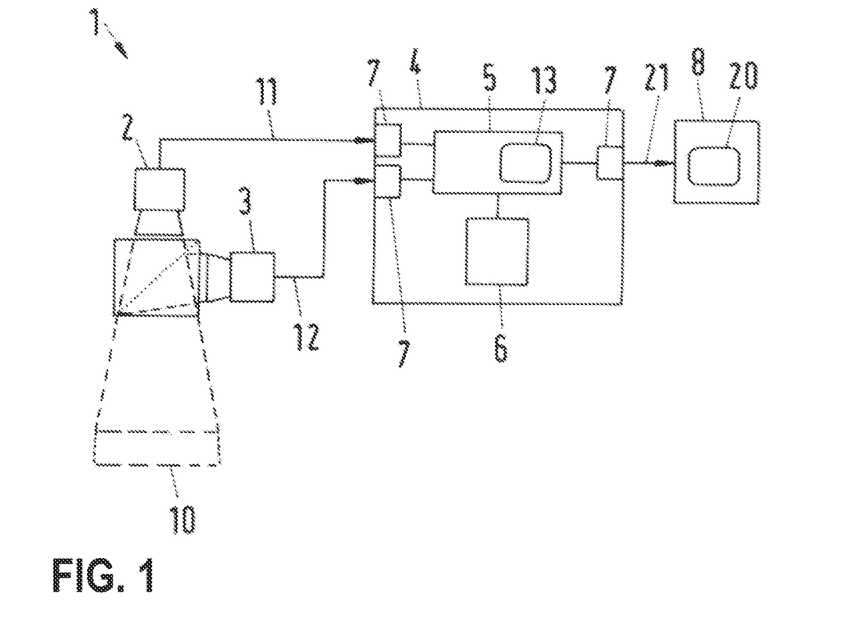
FIG. 1 shows a schematic illustration of the surgical microscope according to an exemplary embodiment of the disclosure.

FIG. 1 shows a schematic illustration of a surgical microscope 1 according to an exemplary embodiment of the disclosure. The surgical microscope 1 includes a camera 2, a fluorescence camera 3 and an evaluation device 4. The surgical microscope 1 is configured to carry out the method described in this disclosure for providing an image representation 20.

The camera 2 is configured to capture a color image representation 11 of the capture region 10. The fluorescence camera 3 is configured to capture a fluorescence image representation 12 of the capture region 10. The regions captured by the camera 2 and the fluorescence camera 3 may in particular also have different sizes provided that a common capture region 10 is present. In particular, the fluorescence camera 3 is sensitive to a wavelength range in which a suitable fluorescence dye emits. In particular, a body part of a patient to be captured (not shown) is arranged in the capture region 10.

The surgical microscope 1 may further include at least one illumination device (not shown), the latter serving to illuminate the capture region 10 and/or the targeted excitation of a fluorescence dye.

In particular, the evaluation device 4 includes at least one computing device 5, for example a microprocessor or a microcontroller, and at least one memory 6. To process the captured color image representation 11 and the captured fluorescence image representation 12, the computing device 5 executes program code, in particular program code stored in the memory 6.

The captured color image representation 11 and the captured fluorescence image representation 12 are supplied to the evaluation device 4 by way of interfaces 7 that are accordingly configured to this end.

The evaluation device 4 is configured to produce or extract a detailed image 13 from the captured color image representation 11 with a spatial filter and an edge stop function. In particular, the spatial filter is a two-dimensional Gaussian spatial filter.

Further, the evaluation device 4 is configured to mix the captured color image representation 11, the captured fluorescence image representation 12 and the produced or extracted detailed image 13 to form a mixed image representation 20.

In this case, provision can be made for the detailed image 13 to be produced by weighted summation of the captured color image representation 11 filtered with the spatial filter and the captured color image representation 11, followed by a subtraction of the summation image representation 11s from the captured color image representation 11, with an output value of the edge stop function being used as weighting parameter.

The mixed image representation 20 is provided in the form of an image signal 21 which encodes the mixed image representation 20. To this end, the evaluation device 4 produces the image signal 21, for example in the form of an analog or digital image signal 21, in particular in the form of a digital data packet. The produced image signal 21 is provided at an interface 7 configured to this end.

The provided image signal 21 can subsequently be output, in particular displayed, on a display device 8 such that a surgeon and/or an assistant is/are able to register the mixed image representation 20.

Provision can be made for the surgical microscope 1 to be in the form of a stereoscopic surgical microscope 1, that is to say it respectively has two channels for capturing the color image representation 11 and the fluorescence image representation 12, for example as described in US 2018/0364470 A1. Then, the method is carried out for each channel such that a separate mixed image representation 20 and a separate image signal 21 is produced and provided for each of the two channels. Provision can be made for a stereoscopic image representation or a stereoscopic image signal (not illustrated) to be produced therefrom.

Figure 2:
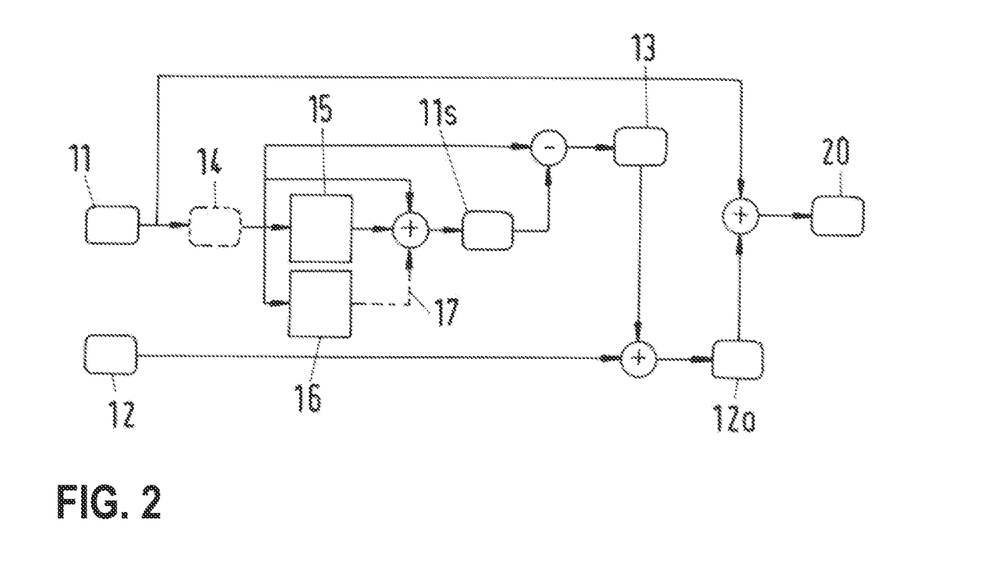
FIG. 2 shows a schematic illustration of a flowchart of the method for the purposes of explaining a method of processing the captured color image representation and the captured fluorescence image representation with the evaluation device according to an exemplary embodiment of the disclosure.

FIG. 2 shows a schematic illustration of a flowchart of an exemplary embodiment of the method, which shows a method of processing the captured color image representation 11 and the captured fluorescence image representation 12 with the evaluation device.

Provision can be made for the evaluation device to be configured to produce an intensity image 14 from the captured color image representation 11, the detailed image 13 being produced from the produced intensity image 14. By way of example, to this end provision can be made for the captured color image representation 11 to be converted into the YCbCr color model and for only the luminance information (i.e., Y) to be subsequently used as intensity information. However, it is also possible in principle to use other intensity values (e.g., also individual color channels of the captured color image representation 11, etc.).

In particular, provision can be made for a logarithmic scale or representation to be used to represent the intensity information from the intensity image 14.

The intensity image 14 is subsequently filtered with a spatial filter 15, which is a two-dimensional spatial filter in particular. In particular, the two-dimensional spatial filter 15 is a two-dimensional Gaussian spatial filter.

A weighting parameter 17 is determined with an edge stop function 16:

$$w_r = \begin{cases} \left(1 - \left(\frac{x}{\lambda}\right)^2\right)^2, & (x \leq \lambda) \\ 0, & (x > \lambda) \end{cases}$$

Here, x is the value of an intensity gradient that is determined with the measure set forth below, in particular at the respective pixel. In this case, the parameter λ allows the sensitivity of the edge stop function 16 to be adjusted, by way of example λ=0.6.

A gradient of the intensity in the intensity image 14 is supplied to the edge stop function 16 via the input value x, in particular pixel-by-pixel (with coordinates x and y):

$$\|\nabla I(x,y)\| = \sqrt{\nabla_x^2(x,y) + \nabla_y^2(x,y)}$$

Subsequently, the captured color image representation 11 or the intensity image 14 and the captured color image representation 11 spatially filtered with the spatial filter 15 or the spatially filtered intensity image 14 are summated or mixed with pixel-by-pixel weightings to form a summation image representation 11s:

$$(1-w_r) \cdot l_f + w_r \cdot l_{nl}$$

Here, $l_f$ is the intensity value from the intensity image 14 of the captured color image representation 11 and $l_{nl}$ is the intensity value from the captured color image representation 11 filtered with the spatial filter 15, in particular the two-dimensional spatial filter, more particularly the two-dimensional Gaussian spatial filter, or from the intensity image 14. In particular, the summation is implemented pixel-by-pixel, the weighting parameter 17 (i.e., $w_r$) being chosen or calculated for the respectively considered pixel.

The summation image representation 11s is subtracted from the captured color image representation 11 or the intensity image 14, the result yielding the detailed image 13.

The detailed image 13 and the captured fluorescence image representation 12 are mixed to form an enriched fluorescence image representation 12a. The captured color image representation 11 and the enriched fluorescence image representation 12a are subsequently mixed, as a result of which the mixed image representation 20 is produced. In particular, the monochromatic enriched fluorescence image representation 12a is converted into a suitable color space or into a suitable color model in the process so that mixing with the captured color image representation 11 is rendered possible.

Figure 3:
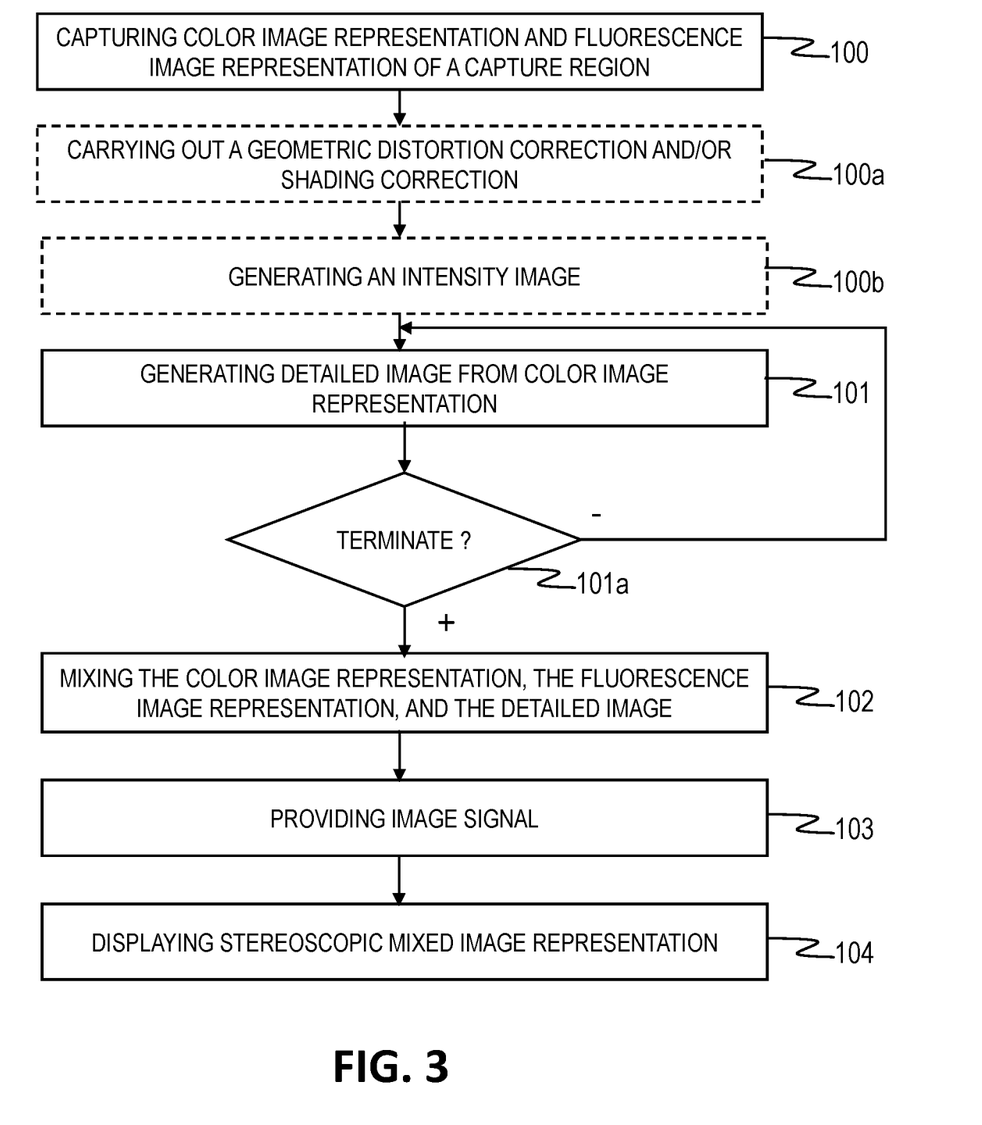
FIG. 3 shows a schematic block diagram of the method for providing an image representation with a surgical microscope according to an exemplary embodiment of the disclosure.

FIG. 3 shows a schematic block diagram of an exemplary embodiment of the method for providing an image representation with a surgical microscope. By way of example, the surgical microscope is a surgical microscope according to the exemplary embodiment shown in FIG. 1.

A color image representation and a fluorescence image representation of a capture region are captured with a camera and with a fluorescence camera, respectively, in a measure 100. By way of example, such a capture region may include a tumor in the brain of a patient, which tumor should be operated on and has been marked with a fluorescence dye.

A detailed image is generated from the captured color image representation with a spatial filter and an edge stop function in a measure 101. In particular, a two-dimensional Gaussian spatial filter can be used to this end.

The captured color image representation, the captured fluorescence image representation and the generated detailed image are mixed to form a mixed image representation in a measure 102.

An image signal which encodes the mixed image representation is provided, in particular generated and/or output, in a measure 103.

In a measure 104, provision can be made for the mixed image representation to be displayed on a display device by virtue of the image signal being supplied to a display device.

In a measure 100a, provision can be made for a geometric distortion correction and/or a shading correction to be carried out for the camera and the fluorescence camera. In particular, the corrections are carried out on the captured color image representation and the captured fluorescence image representation.

In a measure 100b, provision can be made for an intensity image to be generated from the captured (optionally corrected) color image representation, the detailed image being generated from the generated intensity image in measure 101. In particular, provision can be made for the intensity image to be generated and/or processed on a logarithmic scale or in a logarithmic representation.

In measure 101, provision can be made for a position-related value of a gradient of an intensity in the produced intensity image to be used in each case as input parameter of the edge stop function.

In a development, provision can be made in measure 101 for the detailed image to be produced by weighted summation of the captured color image representation filtered with the spatial filter and the captured color image representation, followed by a subtraction of the summation image representation from the captured color image representation, with an output value of the edge stop function being used as weighting parameter.

Further, provision can be made for the production of the detailed image to be repeated iteratively with altered parameters. To this end, measure 101 is repeated until at least one termination criterion has been satisfied or a predetermined number of iterations has been carried out. In this respect, whether the termination criterion has been satisfied or the predetermined number of iterations has been reached is monitored in a measure 101a.

In measure 102, provision can be made, during mixing, for the produced detailed image to be mixed with the fluorescence image representation and for the resultant enriched fluorescence image representation to be mixed with the captured color image representation.

Provision can be made for the method to be carried out on a stereoscopic camera and/or stereoscopic fluorescence camera. To this end, measures 100 to 104 are carried out for each channel of the stereoscopic surgical microscope. As a result, it is possible to make a stereoscopic mixed image representation available and for example display the latter in measure 104.

Figure 4:
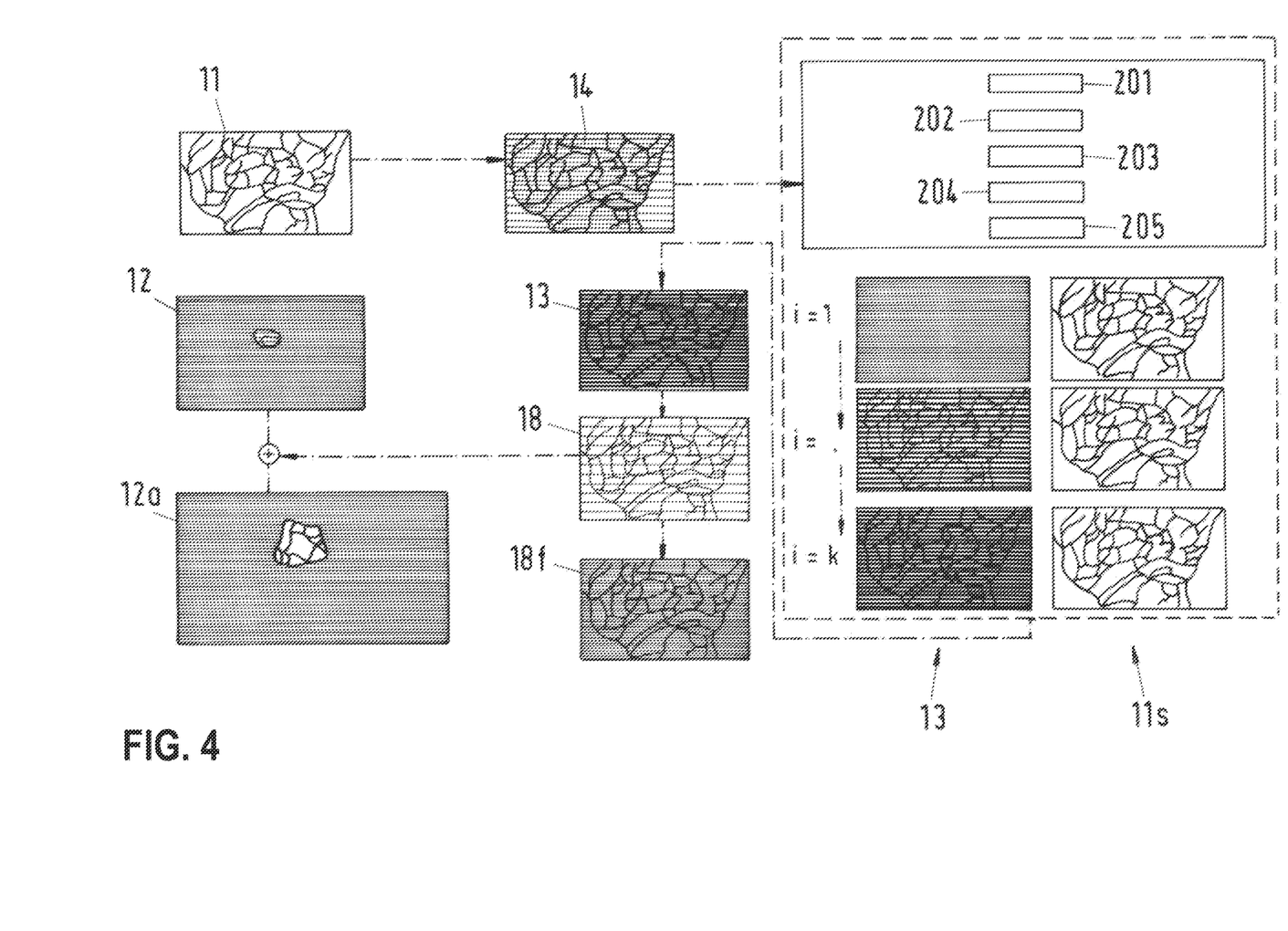
FIG. 4 shows a schematic block diagram for elucidating one exemplary embodiment of the method.

FIG. 4 shows a schematic block diagram for elucidating an exemplary embodiment of the method for providing an image representation with a surgical microscope.

The color image representation 11 of the capture region captured with a camera is converted into a logarithmic intensity image 14. The intensity image 14 is subsequently processed, in particular in a plurality of iterations, in five measures 201 to 205 with the evaluation device 4 of the surgical microscope 1 (FIG. 1).

A two-dimensional spatial filter in the form of a two-dimensional Gaussian spatial filter is applied to the intensity image 14 in measure 201. In particular, this is implemented by an iterative application to the intensity image 14. In this case, a filter variable is chosen with a linearly increasing filter variable ($\sigma_i = i\sigma$), in particular depending on the iteration, where i is the current iteration of a total of k iterations.

A value of a gradient of the intensity in the intensity image 14 is determined in measure 202. The value of the gradient is determined pixel-by-pixel in particular and is required for the edge stop function. An example of a measure for the value of the gradient was already specified above.

A weighted edge stop function is defined in measure 203. By way of the edge stop function it is possible, in particular, to reduce or minimize excessive smoothing effects at the edges as a result of filtering with the Gaussian spatial filter. Whenever the calculated gradient is larger than a predetermined value, a weighting parameter for a summation in measure 204 is set to zero. An example of an edge stop function has already been specified above.

In measure 204, a filtered image representation is produced from the original intensity image 14 and the intensity image 14 that has been filtered with the Gaussian spatial filter, by virtue of the original intensity image 14 and the intensity image 14 that has been filtered with the Gaussian spatial filter being mixed, with weighting, to form a summation image representation 11s, the weighting parameter for each pixel being specified by the edge stop function. An example of the weighted summation for mixing purposes has already been specified above.

In measure 205, the detailed image 13 is generated from the intensity image 14 and the summation image representation 11s produced in measure 204. To this end, the summation image representation 11s is subtracted pixel by pixel from the intensity image 14.

In FIG. 4, this is indicated for a plurality of iterations from 1 to k.

The final detailed image 13 is converted into an absolute detailed image 18. In particular, this is implemented so as to remove negative values which may have originated from the preceding subtraction. In particular, this procedure ensures that no important information is lost when the detailed image 13 (or the absolute detailed image 18) is subsequently mixed with the other image representations 11, 12.

An exemplary MATLAB code for generating the absolute detailed image 18 is shown below:

```
img_detail=img_Y_log-img_baseLayer;

img_detail=img_detail+(abs(min(min(img_detail))/
    10));
```

This absolute detailed image 18 is subsequently mixed with the fluorescence image representation 12 so that an enriched fluorescence image representation 12a arises, the latter subsequently being mixed with the color image representation 11 (not shown, see FIG. 2).

Alternatively, provision can also be made for the absolute detailed image 18 to be converted back into the original color space (e.g., RGB) such that a color detailed image 18f arises, in order to subsequently mix the latter with the color image representation 11 (not shown).

Figure 5:
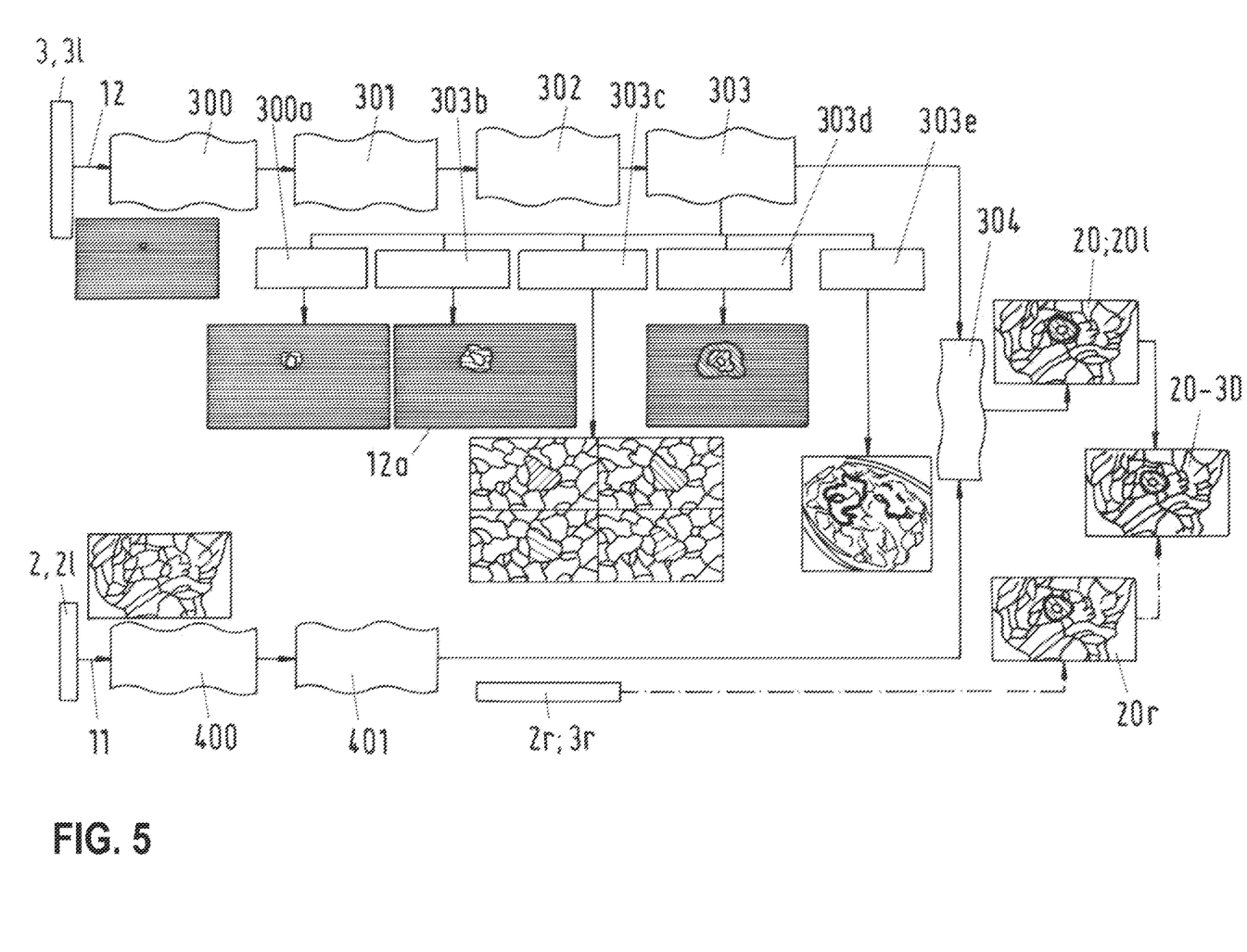
FIG. 5 shows a schematic illustration for elucidating a processing chain in a surgical microscope and the integration of the method described in this disclosure into this processing chain.

FIG. 5 shows a schematic illustration for elucidating a processing chain in a surgical microscope and the integration of the method described in this disclosure for providing an image representation with a surgical microscope into the processing chain. Not all measures need to necessarily be carried out in this context; therefore, some of the measures may also be optional.

Geometric distortion corrections can be carried out on the captured fluorescence image representation 12 and on the captured color image representation 11 in measures 300 and 400. In particular, this is advantageous if an optical arrangement of the camera 2 and the fluorescence camera 3 does not yet or does not completely undertake such a correction.

Shading corrections may be undertaken in measures 301 and 401.

An intensity calibration may be carried out in a measure 302.

An image improvement and/or image enrichment can be carried out in a measure 303. By way of example, this measure 303 may include a measure 303a for improving the contrast. Further, as measure 303b, this measure 303 may include the method described in this disclosure for providing an image representation with a surgical microscope, within the scope of which a detailed image is produced, the latter being used to enrich the captured fluorescence image representation 12 to form an enriched fluorescence image representation 12a. The fluorescence image representation may be color coded in a measure 303c, as a result of which the information from the fluorescence image representation 12 is better identifiable in a mixed image representation 20. To this end, there may also be color coding on the basis of the intensity values ("pseudo-coloring") in a measure 303d. A measure 303e includes the identification and marking of a boundary of a tumor.

The fluorescence image representation 12 processed in this way and the color image representation 11 processed in this way are mixed in a measure 304 to form a mixed image representation 20 (or 20l and 20r). If this is implemented for two channels (right and left), that is to say stereoscopically, it is possible to produce and provide a three-dimensional mixed image representation 20-3D.

An advantage of the method described in this disclosure and of the surgical microscope described lies in an improved provision of a mixed image representation, in which details from a captured color image representation still are easily recognizable, even after mixing with a captured fluorescence image representation.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Surgical microscope
2 Camera
2l Camera (left channel)
2r Camera (right channel)
3 Fluorescence camera
3l Fluorescence camera (left channel)
3r Fluorescence camera (right channel)
4 Evaluation device
5 Computing device
6 Memory
7 Interface
8 Display device 10 Capture region
11 Color image representation
11s Summation image representation
12 Fluorescence image representation
12a Enriched fluorescence image representation
13 Detailed image
14 Intensity image
15 Spatial filter
16 Edge stop function
17 Weighting parameter
18 Absolute detailed image
18f Color detailed image
20 Mixed image representation
20l Mixed image representation (left channel)
20r Mixed image representation (right channel)
20-3D Three-dimensional mixed image representation
21 Image signal
100-104 Measures
201-205 Measures
300-304 Measures
400-401 Measures
i Iteration
k Number of iterations

What is claimed is:

1. A method for providing an image representation with a surgical microscope, the method comprising:
capturing a color image representation of a capture region with a camera;
capturing a fluorescence image representation of the capture region with a fluorescence camera;
generating a detailed image from the color image representation with a spatial filter and an edge stop function;
mixing the color image representation, the fluorescence image representation, and the detailed image to form a mixed image representation; and
providing an image signal which encodes the mixed image representation.

2. The method as claimed in claim 1, further comprising:
generating an intensity image from the color image representation, and
wherein the detailed image is generated from the intensity image.

3. The method as claimed in claim 2, wherein the intensity image is at least one of (a) generated, and (b) processed on a logarithmic scale.

4. The method as claimed in claim 2, wherein a position-related value of a gradient of an intensity in the generated intensity image is provided as an input parameter of the edge stop function.

5. The method as claimed in claim 4, wherein the detailed image is generated by a weighted summation of the color image representation filtered with the spatial filter and the color image representation, followed by a subtraction of a summation image representation from the color image representation, with an output value of the edge stop function being provided as weighting parameter.

6. The method as claimed in claim 1, wherein the spatial filter is a two-dimensional Gaussian spatial filter.

7. The method as claimed in claim 1, wherein generating of the detailed image is repeated iteratively with altered parameters.

8. The method as claimed in claim 1, wherein, during mixing, the detailed image is mixed with the fluorescence image representation and a resultant enriched fluorescence image representation is mixed with the color image representation.

9. The method as claimed in claim 1, further comprising:
carrying out at least one of (a) a geometric distortion correction, and (b) a shading correction for the camera and the fluorescence camera.

10. The method as claimed in claim 1, wherein the method is carried out on at least one of (a) a stereoscopic camera, and (b) a stereoscopic fluorescence camera.

11. A method for providing an image representation for a surgical microscope, the method comprising:
receiving a color image representation of a capture region captured with a camera;
receiving a fluorescence image representation of the capture region captured with a fluorescence camera;
generating a detailed image from the color image representation with a spatial filter and an edge stop function;
mixing the color image representation, the fluorescence image representation, and the detailed image to form a mixed image representation; and
providing an image signal which encodes the mixed image representation.

12. A surgical microscope, comprising:
a camera configured to capture a color image representation of a capture region;
a fluorescence camera configured to capture a fluorescence image representation of the capture region;
an evaluation device configured to:
extract a detailed image from the color image representation with a spatial filter and an edge stop function;
mix the color image representation, the fluorescence image representation, and the extracted detailed image to form a mixed image representation, and
provide an image signal which encodes the mixed image representation.

* * * * *

UNITED STATES PATENT AND TRADEMARK OFFICE
CERTIFICATE OF CORRECTION

PATENT NO. : 12,154,250 B2
APPLICATION NO. : 17/709388
DATED : November 26, 2024
INVENTOR(S) : Dominik Scherer, Senay Karaali and Selamawit Getachew Kelemu

Page 1 of 1

It is certified that error appears in the above-identified patent and that said Letters Patent is hereby corrected as shown below:

On the Title Page

Page 2, Item (56) U.S. PATENT DOCUMENTS change:
"2018/0364470 A1 12/2018 Jauger et al."
To:
"2018/0364470 A1 12/2018 Hauger et al."

Signed and Sealed this
Second Day of September, 2025

Coke Morgan Stewart
*Acting Director of the United States Patent and Trademark Office*